US011090147B2

(12) United States Patent
Spenser

(10) Patent No.: US 11,090,147 B2
(45) Date of Patent: Aug. 17, 2021

(54) SYSTEM FOR UNLOCKING A DEVICE FROM A GUIDE WIRE

(71) Applicant: Cardiovascular Systems, Inc., St. Paul, MN (US)

(72) Inventor: Benjamin Spenser, Hof Karmel (IL)

(73) Assignee: Cardiovascular Systems, Inc., St. Paul, MN (US)

( * ) Notice: Subject to any disclaimer, the term of this patent is extended or adjusted under 35 U.S.C. 154(b) by 369 days.

(21) Appl. No.: 15/763,464

(22) PCT Filed: Oct. 5, 2016

(86) PCT No.: PCT/IL2016/051079
§ 371 (c)(1),
(2) Date: Mar. 27, 2018

(87) PCT Pub. No.: WO2017/060901
PCT Pub. Date: Apr. 13, 2017

(65) Prior Publication Data
US 2018/0280128 A1 Oct. 4, 2018

Related U.S. Application Data

(60) Provisional application No. 62/238,734, filed on Oct. 8, 2015.

(51) Int. Cl.
*A61F 2/01* (2006.01)
*A61M 25/09* (2006.01)
*A61B 17/22* (2006.01)

(52) U.S. Cl.
CPC ............. *A61F 2/011* (2020.05); *A61M 25/09* (2013.01); *A61B 2017/22049* (2013.01);
(Continued)

(58) Field of Classification Search
CPC .. A61F 2/01; A61F 2/011; A61F 2/013; A61F 2002/015; A61B 2017/22049;
(Continued)

(56) References Cited

U.S. PATENT DOCUMENTS 6,537,296 B2   3/2003   Levinson et al.
8,545,533 B2   10/2013  Spenser et al.
(Continued)

FOREIGN PATENT DOCUMENTS

EP   0 415 332   3/1991

OTHER PUBLICATIONS

Extended European Search Report, dated May 15, 2019, in EP Application No. 16853201.8.
(Continued)

*Primary Examiner* — Diane D Yabut
(74) *Attorney, Agent, or Firm* — Barnes & Thornburg LLP; Jeffrey R. Stone

(57) ABSTRACT

Disclosed is a guidewire stop configured to lock a medical device onto a guidewire. The guidewire stop comprises a locking element, an actuator coupled to the locking element and a locking tube, wherein at least a section of the guidewire and at least part of the locking element or actuator pass through the locking tube. Further disclosed is that the locking tube comprises an unlocking element configured to unlock the medical device from the guidewire. The disclosed guidewire stop has at least the following three configurations: —an initial unlocked configuration in which the guidewire stop and the medical device are movable relative to the guidewire; —a first locked configuration in which the guidewire stop and the medical device are not movable relative to the guidewire; and—a first unlocked configuration in which the guidewire stop and the medical device are movable relative to the guidewire.

16 Claims, 6 Drawing Sheets

(52) U.S. Cl.
CPC ............... *A61F 2002/015* (2013.01); *A61M 2025/09125* (2013.01); *A61M 2025/09183* (2013.01)

(58) Field of Classification Search
CPC ........ A61M 25/09; A61M 2025/09125; A61M 2025/09183
See application file for complete search history.

(56) References Cited

U.S. PATENT DOCUMENTS

| | | | |
|---|---|---|---|
| 2001/0041908 A1* | 11/2001 | Levinson | A61B 17/221 606/200 |
| 2004/0111110 A1 | 6/2004 | Melker | |
| 2007/0123913 A1 | 5/2007 | Beulke | |
| 2007/0293719 A1 | 12/2007 | Scopton et al. | |
| 2009/0105653 A1 | 4/2009 | Spenser et al. | |
| 2013/0090626 A1 | 4/2013 | Feldtman | |
| 2014/0155930 A1 | 6/2014 | Bennett et al. | |
| 2014/0358186 A1 | 12/2014 | Frock et al. | |

OTHER PUBLICATIONS

International Search Report of PCT Application No. PCT/IL16/51079 dated Mar. 24, 2017.

\* cited by examiner

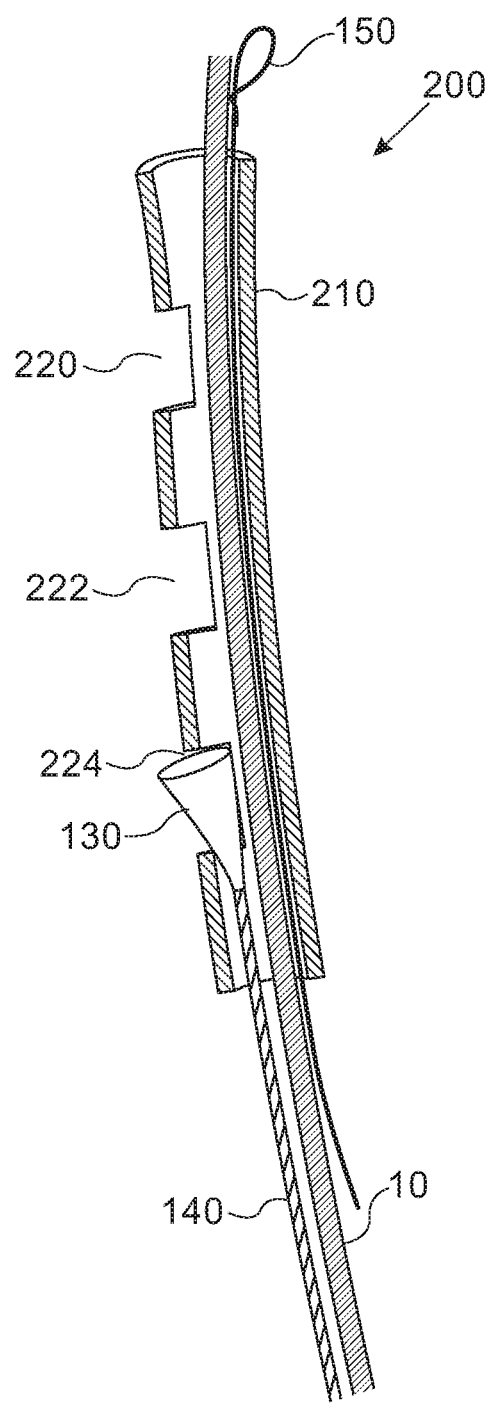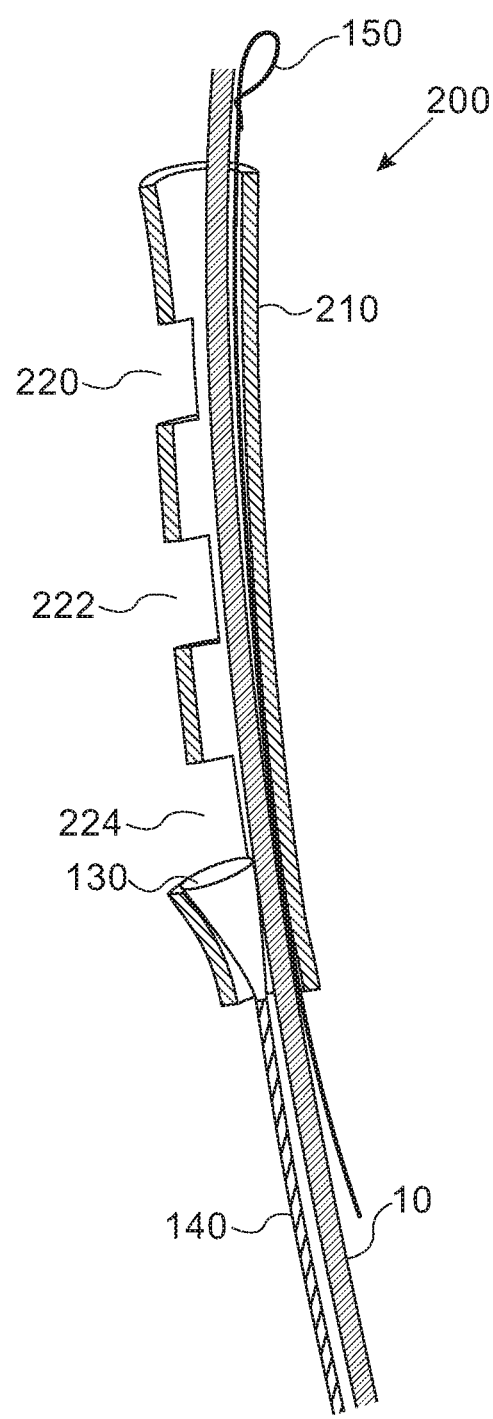
*Fig. 2G*  *Fig. 2H*

SYSTEM FOR UNLOCKING A DEVICE FROM A GUIDE WIRE

CROSS-REFERENCE TO RELATED APPLICATIONS

This application is a National Phase Application of PCT International Application No. PCT/IL2016/051079, International Filing Date Oct. 5, 2016, claiming the benefit of U.S. Provisional Patent Application No. 62/238,734, filed Oct. 8, 2015, all of which are hereby incorporated by reference.

FIELD OF THE INVENTION

This invention is directed to the field of medical procedures in which guidewires are employed. In particular, the present invention is directed to a guidewire stop and release device.

BACKGROUND OF THE INVENTION

Transcatheter procedures are employed in increasing numbers for opening stenosed or occluded blood vessels in patients caused by deposits of plaque or other materials on the walls of the blood vessels. Such minimally invasive procedures have proven to be advantageous in comparison to traditional surgical procedures, such as open heart surgery. For example, stenosis in arteries and other blood vessels can be treated by permanently or temporarily introducing a stent into the stenosed region to open the lumen of the vessel.

However, while implanting a stent or any other prosthetic device, embolic material may be released into the blood stream, placing the patient at great risk. Embolic material formed of calcium deposits, intimal debris, pieces of artheromatous plaque and/or thrombi has the potential of migrating downstream and causing distal tissue damage, for example a stroke or myocardial infarction. Embolic material that can potentially damage the distal tissue is often released during vascular intervention procedures, such as stenting of an artheromatous region.

To alleviate the release of embolic material into the blood stream, an embolic filter may be advanced to a site distal to the treatment site in order to filter and capture undesired embolic material from entering the blood stream. The filter is typically formed from a mesh material mounted on an expansion frame adapted to open from a contracted (or collapsed) configuration to a deployed (or open) configuration. The filter is typically inserted over or together with a guidewire using a delivery catheter. Following the treatment procedure, the filter is collapsed and removed from the body along the guidewire or together with the guidewire. Additional treatment devices, such as balloons and stents, can be inserted and removed via the same guidewire.

Such filters, as described above, should be positioned at a location as close as possible distal of the treatment site to ensure that most or all of the embolic debris is trapped by the filter. On the other hand, the guidewire should extend as far as possible into the body lumen to stabilize the treatment site. It is extremely difficult to achieve both these objectives simultaneously when using a filter that has a fixed position on the wire, since determining the accurate placement of the filter position relative to the treatment site by fluoroscopic observation is very difficult.

Another concern is the difficulty of placing a guide wire in a distal location, especially when the blood vessel is very torturous and occluded. Thus, once the physician manages to place the guide wire properly, it would be preferable to retain the guide wire position throughout the whole procedure without the need to replace it during the procedure, when for example the filter is full, or when a new filter, or other device, is required.

Therefore, there is a need for a guidewire stop and release device capable of being stopped/locked on a bare guidewire, i.e. a guidewire section devoid of a preformed or fixedly attached stop. There is also a need for an intravascular treatment device capable of being stopped and/or locked on the guidewire at any user-selectable position following deployment of the treatment device in the body lumen that is capable of releasing/unlocking the filter so as to retrieve it and replace it without changing the position of the guidewire.

SUMMARY OF THE INVENTION

Embodiments of the invention are directed to a guidewire stop configured to lock a medical device onto a guidewire, the guidewire stop comprising a locking element, an actuator coupled to the locking element and a locking tube and wherein at least a section of the guidewire and at least part of the locking element or actuator pass through the locking tube;
wherein the locking tube comprises an unlocking element configured to unlock the medical device from the guidewire; and
wherein the guidewire stop has at least the following three configurations:
 an initial unlocked configuration in which the guidewire stop and the medical device are movable relative to the guidewire;
 a first locked configuration in which the guidewire stop and the medical device are not movable relative to the guidewire; and
 a first unlocked configuration in which the guidewire stop and the medical device are movable relative to the guidewire.

According to some embodiments, the unlocking element is a hole, fissure, indentation, cavity, orifice, window, gap, dent, cut, puncture or perforation in the locking tube, and wherein the unlocking element has a size and shape allowing the unlocking element and the locking element to be engaged with one another.

According to some embodiments, at least part of the medical device passes through the locking tube. According to some embodiments, the medical device is coupled to at least one element of the guidewire stop. According to some embodiments, the medical device is coupled to the locking tube. According to some embodiments, the locking tube is prepared from a resilient, yielding or springy material.

According to some embodiments, the locking element is a tapered locking element. According to some embodiments, the tapered locking element has a wedge shape. According to some embodiments, the actuator is operatively coupled to a tip portion of the tapered locking element by a separable screw connection.

According to some embodiments, the locking element is moved in the proximal direction to at least one locked configuration and to at least one unlocked configuration by pulling on the actuator in the proximal direction. According to some embodiments, the locking element is moved in the proximal direction by a rotary movement of the actuator. According to some embodiments, the locking element and the actuator are formed as an integral unit. According to some embodiments, the actuator comprises a pulling wire extending in a longitudinal direction. According to some embodiments, the pulling wire comprises a rated break point. According to some embodiments, the pulling wire is uncoupled from the locking element when a pulling force applied longitudinally in a proximal direction exceeds a predetermined value.

According to some embodiments, the medical device is coupled to the locking tube, the locking element, the actuator or any combination thereof. According to some embodiments, the medical device is an embolic filter. According to some embodiments, the locking tube includes more than one unlocking element.

Embodiments of the invention are directed to a guidewire stop configured to lock a medical device onto a guidewire, the guidewire stop comprising a locking element, an actuator coupled to the locking element and a locking tube and wherein at least a section of the guidewire and at least part of the locking element or actuator pass through the locking tube;
characterized by an unlocking element configured to unlock the medical device from the guidewire,
wherein the locking tube comprises the unlocking element; and
wherein the guidewire stop has at least the following three configurations:
  an initial unlocked configuration in which the guidewire stop and the medical device are movable relative to the guidewire;
  a first locked configuration in which the guidewire stop and the medical device are not movable relative to the guidewire; and
  a first unlocked configuration in which the guidewire stop and the medical device are movable relative to the guidewire.

Further embodiments of the invention are directed to a method of replacing a first medical device with a second medical device, wherein the first medical device is locked onto a guidewire at a treatment site by a first guidewire stop comprising a first locking element, a first actuator coupled to the first locking element and a first locking tube, wherein the first locking tube comprises a first unlocking element, the method comprising:
  coupling the locking element with the unlocking element, thereby unlocking the first medical device from the guidewire;
  removing the first medical device from the treatment site along the guidewire;
  introducing the second medical device along the guidewire into the treatment site;
  locking the second medical device onto the guidewire by a second guidewire stop comprising second locking element, a second actuator coupled to the second locking element and a second locking tube, wherein the second locking tube comprises a second unlocking element; and
  when the medical procedure is concluded, coupling the second locking element with the second unlocking element, thereby unlocking the second medical device form the guidewire; and
  removing the second medical device from the treatment site along the guidewire.

According to some embodiments, the second medical device is the first medical device after technically maintained outside of the treatment site. According to some embodiments, the first guide wire stop and the second guidewire stop are the same, such that the first and second locking elements, unlocking elements, locking tubes and actuators are the same. According to some embodiments, the method steps may be repeated any number of times, wherein any number of medical devices may be replaced with any number of additional medical devices and wherein any one of the medical devices may be replaced by the same medical device after the medical device was technically maintained outside of the treatment site.

An actuatable guidewire stop and release device configured to limit movement of a medical device relative to a guidewire having a longitudinal direction, comprising:
the guidewire;
a locking tube having an unlocking element, an interior wall and an external wall disposed about the guidewire and having a locked configuration, wherein the locking tube is prevented from movement relative to the guidewire, and an unlocked configuration, wherein the locking tube is moveable relative to the guidewire;
a tapered locking element having a first end portion constructed as a tip facing the locking tube and a second end portion having a radial dimension sufficiently large to urge the guidewire against the interior wall of the locking tube in the locked configuration, the tapered locking element independently moveable relative to both the guidewire and the locking tube in the unlocked configuration;
an actuator connected to the first end portion of the locking element, wherein upon actuation, the actuator moves the locking element in the longitudinal direction into a radial space between the locking tube and the guidewire and presses the guidewire against a portion of the interior wall of the locking tube that is not in contact with the tapered locking element, thereby placing the locking tube in the locked configuration; and
wherein upon further actuation, the actuator moves the locking element further in the proximal longitudinal direction, thereby engaging the tapered locking element with the unlocking element, thereby placing the locking tube in the unlocked configuration.

A method for securing a guidewire stop and release device along a length of a guidewire having a substantially uniform diameter and defining a longitudinal direction, the guidewire stop and release device comprising a locking tube having an unlocking element and disposed about the guidewire and having a locked configuration, wherein the locking tube is prevented from movement relative to the guidewire, and an unlocked configuration, wherein the locking tube is moveable relative to the guidewire, a tapered locking element having a first end portion constructed as a tip facing the locking tube and a second end portion having a radial dimension sufficiently large to urge the guidewire against an interior wall of the locking tube in the locked configuration, and the tapered locking element independently moveable relative to both the guidewire and the locking tube in the unlocked configuration; and an actuator connected to the first end portion of the locking element, the method comprising the steps of:
with a catheter, advancing the guidewire stop and release device along the guidewire to a desired location;
actuating the actuator in the longitudinal direction so as to draw the locking element into a radial space between the locking tube and the guidewire, thereby pressing the guidewire against a portion of the interior wall of the locking tube that is not in contact with the tapered locking element; placing the locking element in the locked configuration; and
actuating the actuator in the longitudinal direction so as to engage the locking element with the unlocking element, thereby releasing the stop and release device.

According to some embodiments, the method further comprises:
detaching the actuator from the locking element; and withdrawing the actuator in a proximal direction of the guidewire.

According to some embodiments, the actuator comprises a pulling wire, and the step of detaching includes pulling the pulling wire in the proximal direction. According to some embodiments, the actuator threadingly engages the locking element, and the step of detaching includes rotating the actuator relative to the locking element.

BRIEF DESCRIPTION OF THE DRAWINGS

Embodiments of the invention will be understood and appreciated more fully from the following detailed description in conjunction with the figures, which are not to scale, in which like reference numerals indicate corresponding, analogous or similar elements, and in which:

FIG. 2G presents a cross section of an embodiment of a stop and release device of the invention in a third unlocked configuration, wherein the stop and release device shown comprises three unlocking elements;

FIG. 2H presents a cross section of an embodiment of a stop and release device of the invention in a fourth locked configuration, wherein the stop and release device shown comprises three unlocking elements;

DETAILED DESCRIPTION OF THE INVENTION

Figures 1A, 1B, 1C:
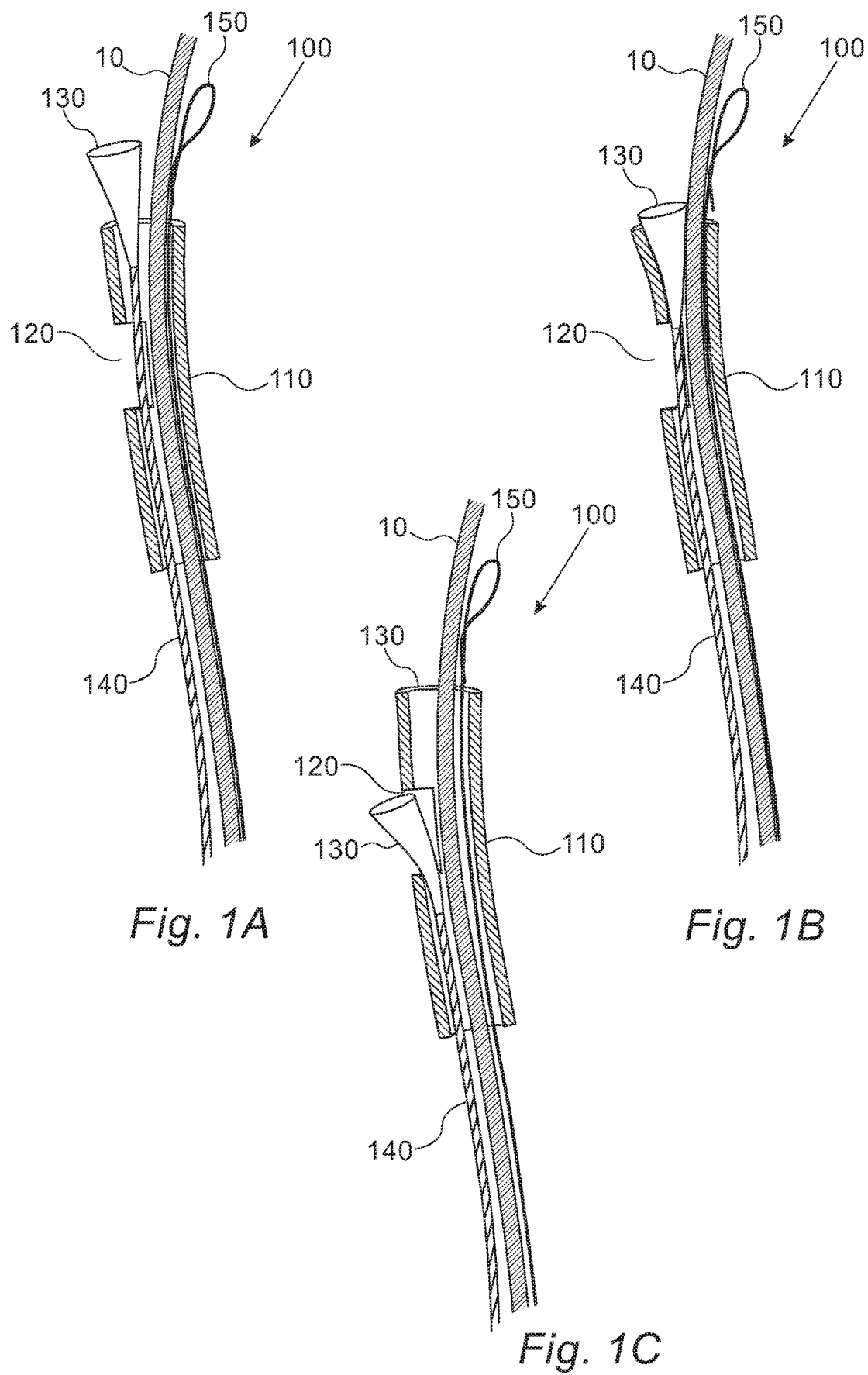
FIG. 1A presents a cross section of an embodiment of a stop and release device of the invention in an initial unlocked configuration, wherein the stop and release device shown comprises one unlocking element.
FIG. 1B presents a cross section of an embodiment of a stop and release device of the invention in a first locked configuration, wherein the stop and release device shown comprises one unlocking element.
FIG. 1C presents a cross section of an embodiment of a stop and release device of the invention in a first unlocked configuration, wherein the stop and release device shown comprises one unlocking element.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Embodiments of the invention are directed to a user-actuatable guidewire stop and release device, wherein the stop and release device is designed to allow a user to stop/lock a medical device at any desired position along a guidewire and, when required, to release/unlock the device, such that it can be moved freely along the guidewire. Thus, the stop and release device of the invention may have at least two configurations, a locked configuration and an unlocked configuration. According to some embodiments, the stop and release device includes more than one locked configuration and/or more than one unlocked configuration.

Particularly, in the locked configuration, the stop and release device does not allow the movement of the stop and release device and the medical device along the guidewire, while in the unlocked configuration, the stop and release device and the medical device are allowed to move along the guidewire. Such a stop and release device allows the user to precisely determine the placement of the medical device, possibly after the guidewire was already introduced into the body and further, since comprising at least one unlocked configuration, allows the user to remove/displace the medical device when required, without requiring the simultaneous removal/displacement of the guidewire.

It is noted that throughout, unless specifically mentioned otherwise or unless a person skilled in the art would understand otherwise, the terms "stop" and "release" are interchangeable with the terms "lock" and "unlock", respectively. The term "guidewire" as employed in the present disclosure is intended to refer to any elongated member having a longitudinal direction that is used to facilitate the advancement of other elements through body lumens and into treatment sites in the body. The guidewire may be any standard, non-dedicated guidewire known in the art. It is noted that when the stop and release device is in the locked configuration, the proximal length of the guidewire, which is proximal to the position of the lock and release device on the guidewire, is available for use for any other purpose or additional medical devices. It is further noted that the terms "actuatable guidewire stop", "guidewire stop" and "stop and release device" are interchangeable herein when the guidewire stop comprises an unlocking element, unless specifically mentioned otherwise, or unless a person skilled in the art would understand that the two terms define different devices. In addition, it is noted that throughout the replacement of medical devices includes the removal and insertion of the same medical device along the guidewire, particularly when it is required to maintain the medical device outside of the treatment site, e.g., to clean the filter, e.g., when the medical device is an embolic filter, and the like.

According to some embodiments, the stop and release device has an initial unlocked configuration, at least one locked configuration and at least one unlocked configuration, and includes

- a locking tube, through which at least part of the guidewire passes;
- a locking element, positioned, at least partially, between the locking tube and the guidewire in at least one locked configuration;
- an unlocking element; and
- an actuator coupled to the locking element, wherein the operation of the actuator switches the stop and release device from at least one locked configuration to at least one unlocked configuration.

According to some embodiments, in the locked configuration, the locking tube is prevented from moving relative to the guidewire, while in the unlocked configuration, the locking tube is movable relative to the guidewire. It is noted (as shown clearly in the Figures) that the locking tube has an exterior wall and an interior wall as well as an interior volume having a longitudinal direction, wherein the guidewire, medical device, locking element and/or actuator pass through the interior volume in the longitudinal direction. Thus, in all instances where the passing of elements through the locking tube are detailed herein, it should be understood that those elements pass through the interior volume of the tube in the longitudinal direction. It is further clear that in the locked configuration, friction is formed between the interior wall of the locking tube and the elements passing therethrough.

According to some embodiments, after entering into a first locked configuration, the locking element can move only in the proximal direction, thus, once moved from the initial unlocked configuration to the first locked configuration, the locking element cannot move back to the initial unlocked configuration; rather, it can only move in the proximal direction, to a first unlocked configuration. According to further embodiments, the stop and release device includes multiple unlocking elements, wherein the locking element is designed to move from one unlocking element to the next, in the proximal direction and is prevented from moving in the distal direction from one unlocking element to the previous one. According to such embodiments, the stop and release device includes multiple locked and unlocked configurations, wherein those configurations are consecutive in the sense that the locking element may move only in the proximal direction from a first initial unlocked configuration, to a first locked configuration, to a first unlocked configuration, to a second locked configuration, to a second unlocked configuration, to a third locked configuration, to a third unlocked configuration and so forth. Although three locked and unlocked configurations are exemplified, it is noted that the stop and release device may include any number of locked and unlocked configurations, such as one, two, three, four, five or more locked and/or unlocked configurations. Similarly, the stop and release device may include any appropriate number of unlocking elements, such as one, two, three, four, five or more unlocking elements.

According to some embodiments, in at least one locked configuration, frictional engagement between the locking element, the locking tube, possibly the medical device, and the guidewire prevents the movement of the locking tube along the guidewire. According to some embodiments, when the locking element is engaged with an unlocking element, the frictional engagement between the locking element, the locking tube, possibly the medical device, and the guidewire is released, at least to an extent, allowing the stop and release device, as well as the medical device, to move freely along the guidewire. It is noted that the medical device may be inserted into the treatment site using a medical device holder, such as a wire, a catheter and the like. Accordingly, the medical devices referred to herein are defined to include the medical device holder, unless specifically mentioned otherwise or unless a person skilled in the art would understand otherwise. Particularly, it is possible that the locking tube locks on to the medical device holder, not the medical device itself, however, since the medical device is defined herein to include the medical device holder, the locking tube will be defined to lock on the medical device. According to some embodiments, the medical device is coupled to the locking tube and therefore, when the locking tube is locked in place, the medical device is also locked in place, even if the medical device itself is not frictionally engaged with the guidewire.

Further embodiments of the invention are directed to a method of locking and unlocking a stop and release device, as described herein, on a guide wire, wherein the method includes:

introducing a guidewire into the treatment site;

advancing a medical device and a stop and release device, as detailed herein, along the guidewire, wherein the stop and release device is in an initial unlocked configuration;

locking the medical device onto the guidewire by operating the actuator and switching the stop and release device from the initial unlocked configuration to a first locked configuration;

performing medical operations using the medical device when locked onto the guidewire in the first locked configuration;

unlocking the stop and release device and the medical device from the guidewire by operating the actuator and switching the stop and release device from the first locked configuration to a first unlocked configuration by engaging the locking element with a first unlocking element; and moving the medical device along the guidewire, as required.

According to some embodiments, the method further comprises locking the medical device onto the guidewire by operating the actuator and switching the stop and release device from the first unlocked configuration to a second locked configuration;

performing medical operations using the medical device when locked onto the guidewire in the second locked configuration;

unlocking the stop and release device and the medical device from the guidewire by operating the actuator and switching the stop and release device from the second locked configuration to a second unlocked configuration by engaging the locking element with a second unlocking element; and moving the medical device along the guidewire, as required.

According to some embodiments, the above steps are repeated with additional locked/unlocked configurations and unlocking elements, as required.

According to some embodiments, once unlocked, the medical device is moved along the guidewire and removed from the body, without removing the guidewire. According to some embodiments, once the medical device is removed, the guidewire is removed as well. According to some embodiments, after the medical device is removed, additional devices and/or the same device, after performing any appropriate type of maintenance, may be advanced into the treatment site along the guidewire, locked in place, utilized as necessary, and then unlocked and moved/removed when required. Thus, similar procedures may be repeated numerous times, while the guidewire remains in place.

According to some embodiments, the medical device is an embolic protection device, a blood clot trap, a balloon, or any other intravascular treatment device. According to some embodiments, the medical device is a urological, neurological or cardiological device. According to some embodiments, the medical device may be implanted temporarily or permanently into a body lumen or treatment site. According to some embodiments, the method includes aspirating blood through a guiding catheter, which is introduced into the treatment site along the guidewire, wherein the guiding catheter is coupled to a proximal aspiration system that includes an inflatable balloon, intended to stop blood flow.

According to some embodiments, the stop and release device and/or the medical device may be advanced/retracted along the guidewire, to a desired location, using a catheter. According to some embodiments, the movement of the guidewire, the stop and release device and/or the medical device, may be monitored using any appropriate means, such as fluoroscopic means, utilizing radiopaque markers.

According to some embodiments, the locking tube may be prepared from any appropriate resilient, springy or yielding material, allowing at least a slight deformation or expansion of the locking tube, e.g., when the locking element is, as least partially, wedged into the locking tube, preventing the movement of the stop and release device and the medical device along the guidewire. According to some embodiments, the locking tube is prepared from stainless steel, nitinol, a polymer or any combination thereof. According to some embodiments, the locking tube may include structural elements, such as grooves, spirals and/or multifilar structures.

According to some embodiments, the locking element may be a tapered locking element, such as a wedge, a conical member, a pyramid member, a spring, such as a conical helical spring, and the like. According to embodiments wherein the locking element is a tapered locking element, the tapered locking element is positioned such that the wider end thereof is in the distal direction, while the narrower end thereof is placed in the proximal direction. Particularly, the locking element may be a tapered locking element, having a first end portion constructed as a tip facing in the proximal direction and a second end portion having a radial dimension sufficiently large to lock the stop and release device when wedged against the guidewire, as detailed herein. When referring herein to a first end portion constructed as a tip, it is noted that the tip may end in a point or may be, to a certain degree, cut at any appropriate angle at the end, having a relatively small radial dimension. Further, as defined herein, the radial dimension of the end of the tip and/or the second end portion of the tapered locking element may be an approximation of the radius, since neither the first end portion not the second end portion are required to be perfect circles. In this respect it is noted that any one of the first end portion and the second end portion may include any sides, cut edges, and like, provided that the shape of the locking element is such that it may be used to lock and unlock the stop and release device, as detailed herein.

According to some embodiments, the length of the tapered locking element is between about 3-8 mm. According to some embodiments, the first end portion, e.g., the tip of the tapered locking element, has approximately the same diameter as the actuator to which it is attached, e.g., between about 0.15-0.2 mm. According to +some embodiments, the second end portion of the tapered locking element has a diameter of between about 0.3-1.5 mm. The internal diameter of the locking tube is such that the tapered locking may both lock and unlock the stop and release device, as detailed herein.

According to some embodiments, the locking element includes a recess adapted to receive the guidewire, possibly reducing the overall diameter of the locking tube. According to some embodiments, the locking element may be prebiased to engage the guidewire and disengage from the guidewire when the locking element is pulled into the locking tube.

According to some embodiments, the surface of the locking element is, at least partially, roughened, in order to enhance friction between the locking element and the locking tube and/or the guidewire. Thus, according to some embodiments, the locking element includes a friction generating surface component. The friction generating component may include glass particles, diamond dust, silica, carbon, any other type of abrasive powder or any combination thereof. According to some embodiments, the locking element includes a corrugated surface of any type, including lines, notches, teeth, wedges, hooks and the like, enhancing friction, as detailed herein.

According to some embodiments, the locking element includes a friction reducing coating, such as a gel composition, polytetrafluoroethylene, a hydrophilic coating, a lubricant or any combination thereof, allowing locking element to easily slide into place along the guidewire and to easily move from the initial unlocked configuration to the first locked configuration, to a first unlocked configuration to a second locked configuration and so on. According to some embodiments, the friction reducing coating may be redistributed as necessary, possibly exposing a friction generation surface component, such that, when in a locked configuration, movement along the guidewire is prevented, as detailed herein.

Incorporated herein by reference are embodiments of locking elements presented in FIGS. 7A, 7B, 8A, 8B, 9A, 9B, 9C, 10A, 10B, 10C and 10D of U.S. Pat. No. 7,819,844, all of which may be used according to this invention. According to some embodiments, the interior wall of the locking tube may include any of the surface elements described regarding the locking element.

According to some embodiments, the actuator may be detached from the locking element and withdrawn in the proximal direction, e.g., along the guidewire, via a catheter and the like. Once detached from the actuator, the locking element may remain in place if in a locked configuration, permanently attaching the stop and release device and any medical device present, to the guidewire. Accordingly, if required to remove the stop and release device and/or the medical device from the treatment site separately from the guidewire, the actuator may remain attached to the locking element and may further be used to remove the stop and release device from the treatment site when it is in an unlocked configuration.

According to some embodiments, the actuator may be a pulling wire. According to some embodiments, the locking element and the actuator are formed as a single integral unit. According to some embodiments, the actuator may include a rated break point, which may be placed in close proximity to the locking element, allowing the detachment of the actuator from the locking element.

According to some embodiments, the actuator may be operatively coupled to the locking element by a separable screw connection. In yet another embodiment, the locking element may be moved into frictional engagement with, at least, the guidewire by a rotary movement of the actuator.

According to some embodiments, the actuator may be disconnected from the locking element through user activation and subsequently withdrawn from the body lumen or treatment site. The actuator, e.g., pulling wire, generally separates from the locking element when a pulling force applied longitudinally in a proximal direction exceeds a predetermined value.

Embodiments of the invention are directed to a stop and release device configured to stop and/or release a medical device, when required, relative to a guidewire, wherein the stop and release device comprises a locking element, an actuator coupled to the locking element and a locking tube including at least one unlocking element, wherein at least a section of the guidewire and at least part of the locking element or actuator pass through the locking tube; and wherein the stop and release device has at least the following three configurations:
  an initial unlocked configuration in which the stop and release device and the medical device are movable relative to the guidewire;
  a first locked configuration in which the stop and release device and the medical device are not movable relative to the guidewire; and
  a first unlocked configuration in which the stop and release device and the medical device are movable relative to the guidewire.

According to some embodiments, the unlocking element is a hole, fissure, indentation, cavity, orifice, window, gap, dent, cut, puncture or perforation in the locking tube, and wherein the unlocking element has a size and shape allowing the unlocking element and the locking element to be engaged with one another.

According to some embodiments, at least part of the medical device passes through the locking tube. According to some embodiments, the locking element is moved in the proximal direction to at least one locked configuration and to at least one unlocked configuration by pulling on the actuator in the proximal direction. According to some embodiments, the locking element is moved in the proximal direction by a rotary movement of the actuator. According to some embodiments, the actuator comprises a pulling wire extending in a longitudinal direction. According to some embodiments, the pulling wire is uncoupled from the locking element when a pulling force applied longitudinally in a proximal direction exceeds a predetermined value. According to some embodiments, the medical device is coupled to the locking tube, the locking element, the actuator or any combination thereof. According to some embodiments, the medical device is an embolic filter.

Embodiments of the invention are directed to a method of locking and unlocking a stop and release device on a guide wire, the method comprising:
  introducing a guidewire into a treatment site;
  advancing a medical device and the stop and release device, according to claim 1, along the guidewire, wherein the stop and release device is in an initial unlocked configuration;
  locking the medical device onto the guidewire by operating the actuator and switching the stop and release device from the initial unlocked configuration to a first locked configuration;
  performing medical operations using the medical device when locked onto the guidewire in the first locked configuration;
  unlocking the stop and release device and the medical device from the guidewire by operating the actuator and switching the stop and release device from the first locked configuration to a first unlocked configuration by engaging the locking element with a first unlocking element; and
  moving the medical device along the guidewire, as required.

According to some embodiments, the method further comprises:
  locking the medical device onto the guidewire by operating the actuator and switching the stop and release device from the first unlocked configuration to a second locked configuration;
  performing medical operations using the medical device when locked onto the guidewire in the second locked configuration;
  unlocking the stop and release device and the medical device from the guidewire by operating the actuator and switching the stop and release device from the second locked configuration to a second unlocked configuration by engaging the locking element with a second unlocking element; and
  moving the medical device along the guidewire.

According to some embodiments, the steps of the above method are repeated with additional locked and unlocked configurations and unlocking elements. According to some embodiments, the method further comprises removing the stop and release device, the medical device, or both, from the treatment site when the stop and release device is in an unlocked configuration, while the guidewire remains in the treatment site.

Reference is now made to FIG. 1A, presenting a cross section of an embodiment of stop and release device 100 in an initial unlocked configuration. As shown in FIG. 1A, guidewire 10 passes through locking tube 110, which includes unlocking element 120. As further shown in FIG. 1A, medical device 150 (not fully shown) and locking element 130, coupled to actuator 140, pass, at least partially, through locking tube 110. In the initial unlocked configuration shown in FIG. 1A, locking element 130/actuator 140, locking tube 110 and medical device 150 may freely move along guidewire 10.

Reference is now made to FIG. 1B, presenting a cross section of an embodiment of stop and release device 100 in a first locked configuration. As shown in FIG. 1B, locking element 130 may be moved in the proximal direction, e.g., by pulling on actuator 140, such that locking element 130 is at least partially wedged into locking tube 110, causing friction between locking tube 110, locking element 130, medical device 150 and guidewire 10, such that locking tube 110, locking element 130 and medical device 150 are locked onto guidewire 10, i.e., are prevented from freely moving along guidewire 10.

In order to unlock stop and release device 100, as shown in FIG. 1C, locking element 130 may be further moved in the proximal direction, e.g., by pulling on actuator 140, such that locking element 130 is engaged with unlocking element 120, thereby reducing the frictional forces between locking tube 110, locking element 130, medical device 150 and guidewire 10, and allowing locking tube 110, locking element 130 and medical device 150 to move freely along guidewire 10. Thus, the configuration shown in FIG. 1C is a first unlocked configuration.

Although not shown, it would be understood by the familiar with the art, that moving locking element 130 further in the proximal direction would again wedge locking element at least partially in locking tube 110 in a second locked configuration, such that locking tube 110, locking element 130 and medical device 150 are prevented from freely moving along guidewire 10. Further, although not shown in the figures, pulling locking element 130 in the proximal direction until released from locking tube 110, essentially unlocks stop and release device 100 in a non-reversible manner. Further, although not shown in the Figures, medical device 150 may be coupled to locking tube 110, such that when the movement of locking tube 110 is prevented or allowed along guidewire 10, the movement of medical device 150 is also prevented or allowed, respectively.

Reference is now made to FIGS. 2A, 2B, 2C, 2D, 2E, 2F, 2G and 2H, depicting cross sections presenting various configurations of stop and release device 200, comprising locking tube 210, which includes three unlocking elements 220, 222 and 224. It is noted that although an embodiment of locking tube 210 including three unlocking elements 220, 222 and 224 is shown, any feasible number of such unlocking elements may be included in locking tube 210, such as two, three, four, five or more unlocking elements. It is further noted that although shown is an embodiment where medical device 150 and locking tube 210 are separate entities, they may be coupled to one another, as detailed herein, such that when the movement of locking tube 210 along guidewire 10 is prevented/allowed, the movement of medical device 150 along guidewire 10 is also prevented/allowed, respectively.

Figure 2A:
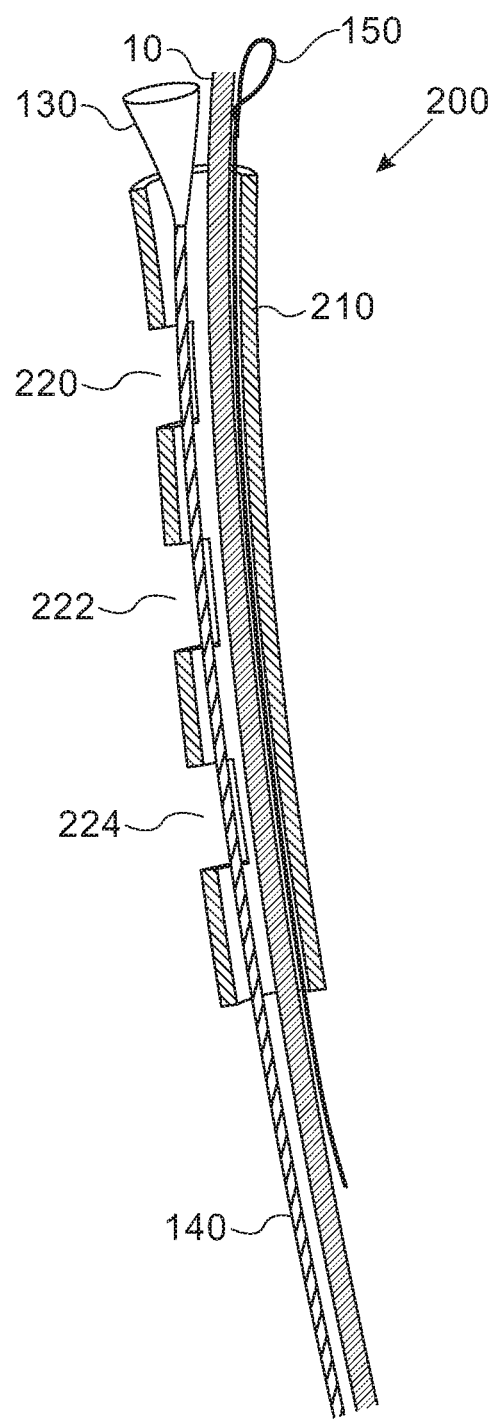
FIG. 2A presents a cross section of an embodiment of a stop and release device of the invention in an initial unlocked configuration, wherein the stop and release device shown comprises three unlocking elements.

FIG. 2A presents the cross section of an initial unlocked configuration of stop and release device 200, in which guidewire 10 passes through locking tube 210, which includes unlocking elements 220, 222 and 224. As shown in FIG. 2A, medical device 150 (not fully shown) and locking element 130, coupled to actuator 140, pass, at least partially, through locking tube 210. In the initial unlocked configuration shown in FIG. 2A, locking element 130/actuator 140, locking tube 210 and medical device 150 may freely move along guidewire 10.

Figure 2B:
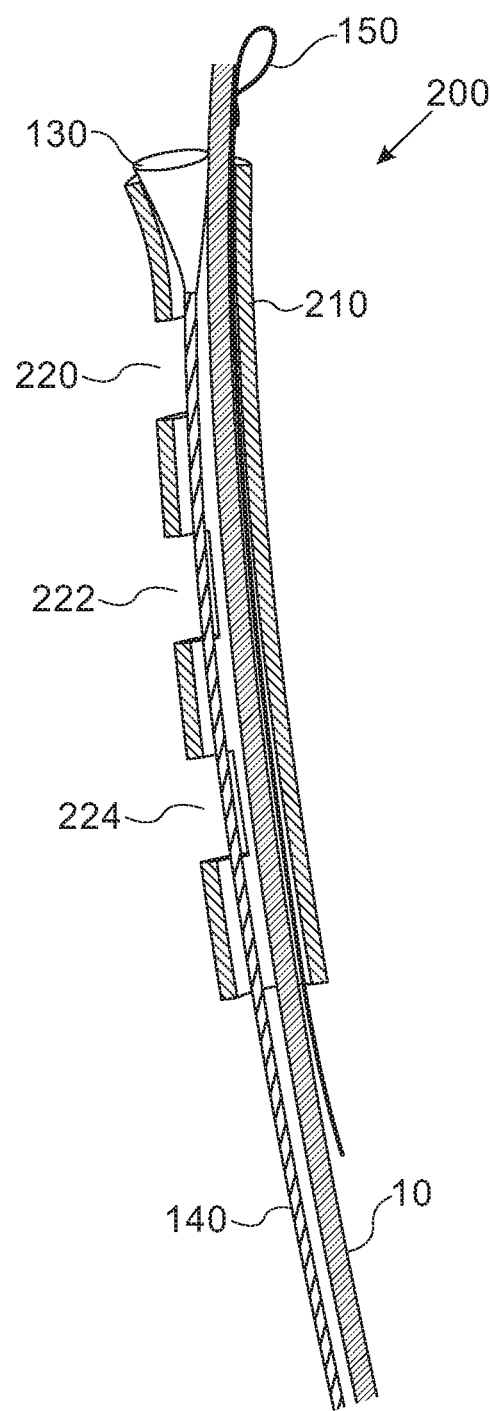
FIG. 2B presents a cross section of an embodiment of a stop and release device of the invention in a first locked configuration, wherein the stop and release device shown comprises three unlocking elements.

Similarly as described above regarding FIG. 1B, FIG. 2B presents a cross section of an embodiment of stop and release device 200 in a first locked configuration. As shown in FIG. 2B, locking element 130 may be moved in the proximal direction, e.g., by pulling on actuator 140, such that locking element 130 is at least partially wedged into locking tube 210, causing friction between locking tube 210, locking element 130, medical device 150 and guidewire 10, such that locking tube 210, locking element 130 and medical device 150 are locked onto guidewire 10, i.e., are prevented from freely moving along guidewire 10.

Figure 2C:
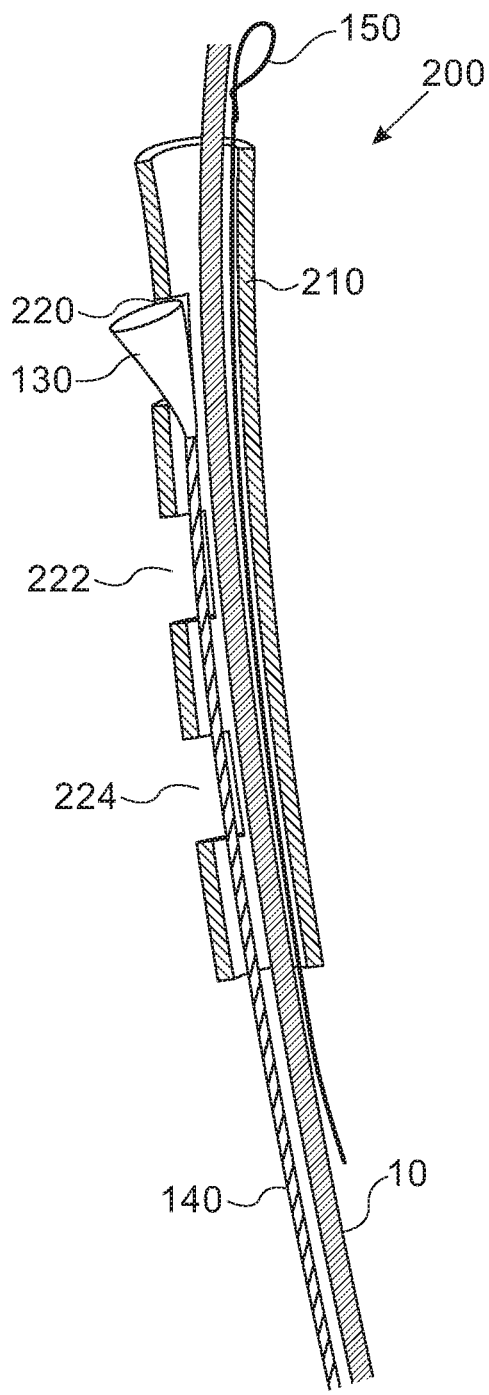
FIG. 2C presents a cross section of an embodiment of a stop and release device of the invention in a first unlocked configuration, wherein the stop and release device shown comprises three unlocking elements.

In order to unlock stop and release device 200, as shown in FIG. 2C, locking element 130 may be further moved in the proximal direction, e.g., by pulling on actuator 140, such that locking element 130 is engaged with unlocking element 220, thereby reducing the frictional forces between locking tube 210, locking element 130, medical device 150 and guidewire 10 and allowing locking tube 210, locking element 130 and medical device 150 to move freely along guidewire 10. Thus, the configuration shown in FIG. 2C is a first unlocked configuration.

Figure 2D:
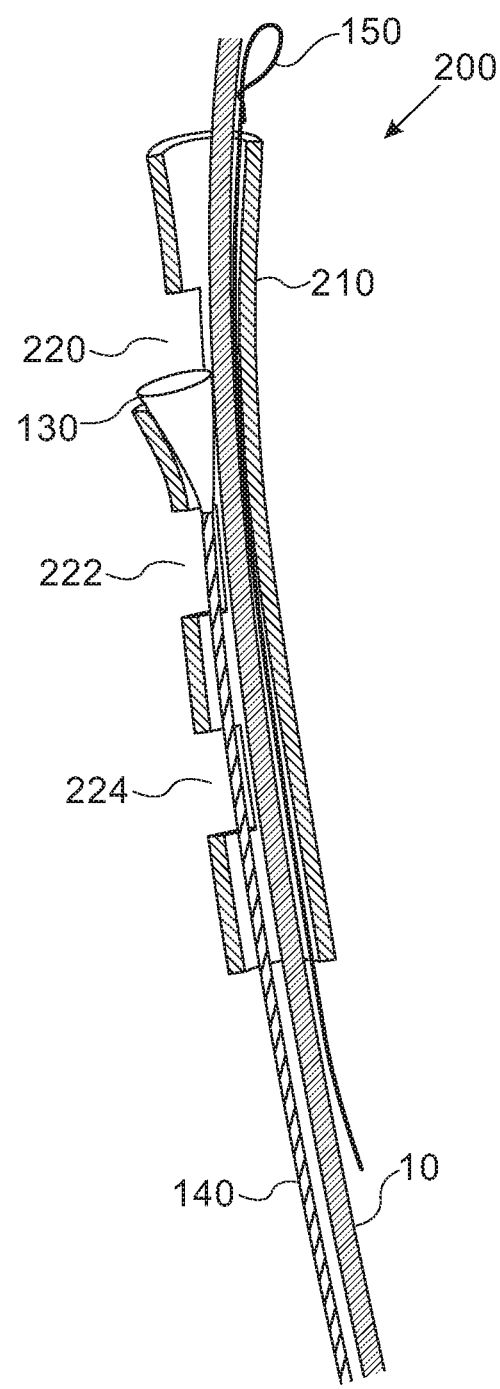
FIG. 2D presents a cross section of an embodiment of a stop and release device of the invention in a second locked configuration, wherein the stop and release device shown comprises three unlocking elements.

As noted above, locking element 130 cannot be moved in the distal direction, only in the proximal direction and therefore; if after stop and release device is placed in the first unlocked configuration (shown in FIG. 2C), it is required again to lock stop and release device 200 on guidewire 10, locking element 130 may be moved in the proximal direction until reaching the second locked configuration shown in FIG. 2D. As shown in FIG. 2D, similarly to FIG. 2B, locking element 130 may be moved in the proximal direction to a section of locking tube 210 that is proximal to unlocking element 220, e.g., by pulling on actuator 140, such that locking element 130 is at least partially wedged into locking tube 210, causing friction between locking tube 210, locking element 130, medical device 150 and guidewire 10, such that locking tube 210, locking element 130 and medical device 150 are locked onto guidewire 10, i.e., are prevented from freely moving along guidewire 10.

Figure 2E:
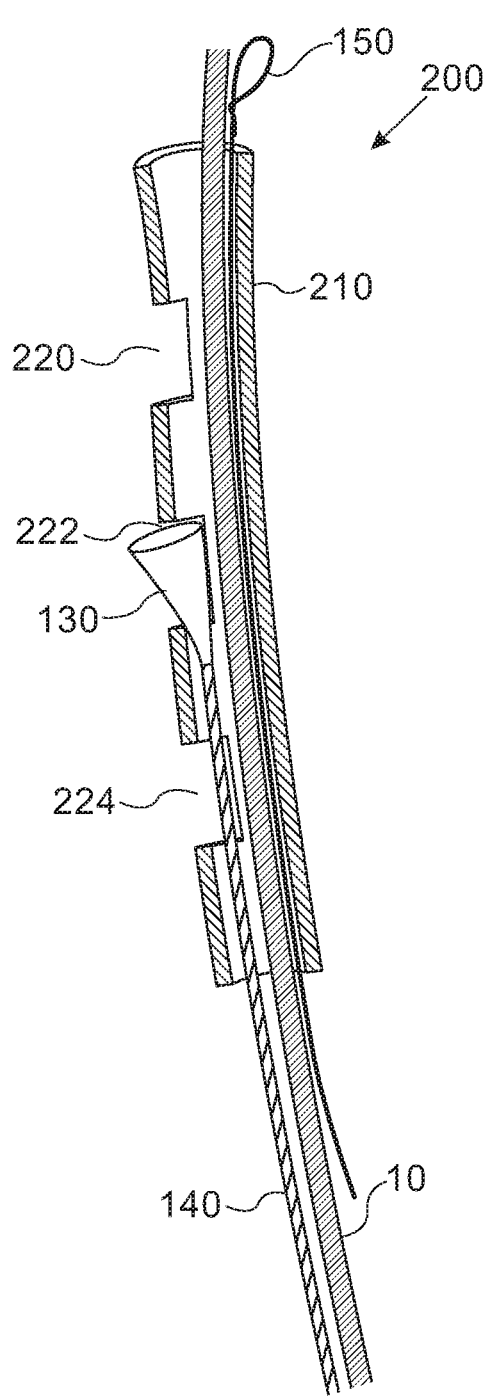
FIG. 2E presents a cross section of an embodiment of a stop and release device of the invention in a second unlocked configuration, wherein the stop and release device shown comprises three unlocking elements.

The same sequence of moving locking element 130 in the proximal direction, e.g., by pulling on actuator 140 in the proximal direction, may be repeated, e.g., by engaging locking element 130 with unlocking element 222, thereby placing stop and release device 200 in a second unlocked configuration, as shown in FIG. 2E. Further locking of stop and release device 200, i.e., placing stop and release device 200 in a third locked configuration, may be achieved by moving locking element 130 further in the proximal direction, e.g., by pulling on actuator 140 in the proximal direction, until locking element 130 is at least partially wedged into a section of locking tube 210 that is proximal to unlocking element 222, as shown in FIG. 2F.

Figure 2F:
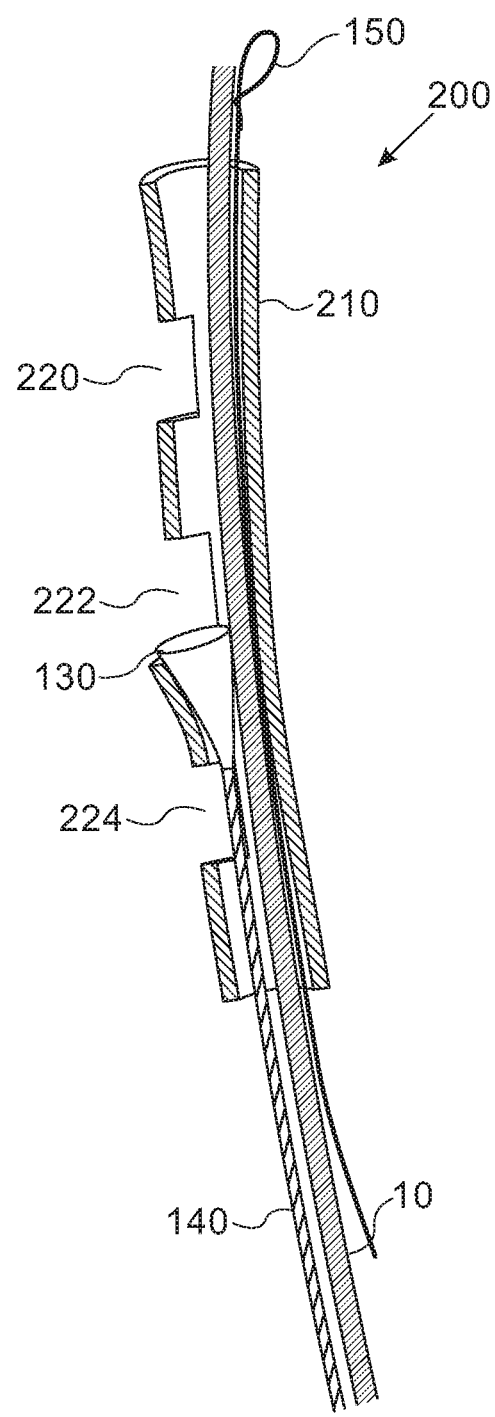
FIG. 2F presents a cross section of an embodiment of a stop and release device of the invention in a third locked configuration, wherein the stop and release device shown comprises three unlocking elements.

After stop and release device 200 is positioned in a third locked configuration, as shown in FIG. 2F, locking element 130 may be further moved in the proximal direction, e.g., by pulling on actuator 140 in the proximal direction, until locking element 130 is engaged with unlocking element 224, placing stop and release device 200 in a third unlocked configuration, as shown in FIG. 2G.

Finally, if locking stop and release device 200 is further required, locking element 130 may be further moved in the proximal direction, e.g., by pulling on actuator 140 in the proximal direction, until locking element 130 is at least partially wedged into a section of locking tube 210 that is proximal to unlocking element 224, as shown in FIG. 2H, presenting a fourth locked configuration of stop and release device 200.

Although not shown in the figures, further pulling locking element 130 in the proximal direction would release locking element 130 from locking tube 210, essentially unlocking stop and release device 200 in a non-reversible manner.

Figure 3A:
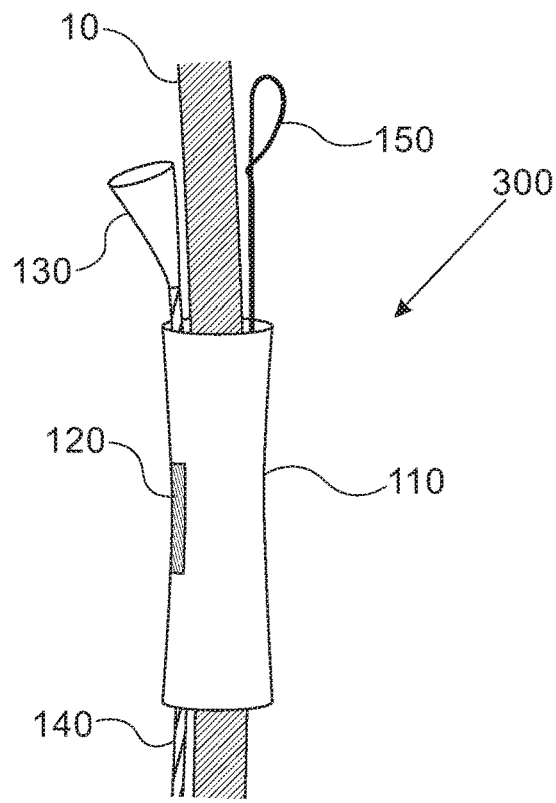
FIG. 3A presents an embodiment of the stop and release device of the invention in which the medical device is coupled to the locking tube.

Reference is now made to FIG. 3A, presenting stop and release device 300, in which medical device 150 is coupled to locking tube 110. Thus, when locking element 130 is wedged into locking tube 110, e.g., by pulling on actuator 140, locking tube 110 is locked onto guidewire 10, automatically locking medical device 150 in place as well, since it is coupled to locking tube 110, which is prevented from moving along guidewire 10. Further, when locking element 130 is engaged with unlocking element 120, thereby unlocking locking tube 110 from guidewire 10, medical device 150 is automatically unlocked as well, since it is coupled to locking tube 110.

Figure 3B:
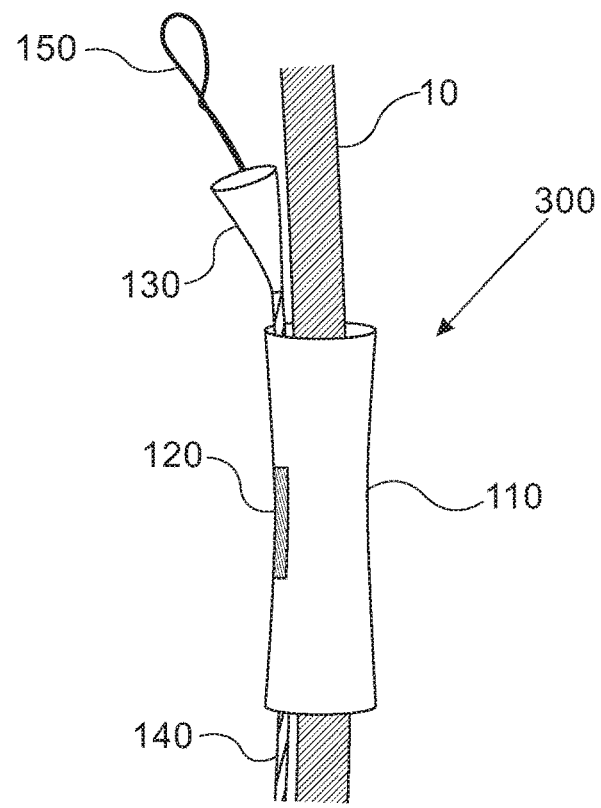
FIG. 3B presents an embodiment of the stop and release device of the invention is which the medical device is coupled to the locking element.

Reference is now made to FIG. 3B, presenting stop and release device 350, in which medical device 150 is coupled to locking element 130. Thus, when locking element 130 is wedged into locking tube 110, e.g., by pulling on actuator 140, locking tube 110 is locked onto guidewire 10, automatically locking medical device 150 in place as well, since it is coupled to locking element 130, which is also prevented from moving along guidewire 10. Further, when locking element 130 is engaged with unlocking element 120, thereby unlocking locking tube 110 from guidewire 10, medical device 150 is automatically unlocked as well, since it is coupled to locking element 130, which may move, together with locking tube 110, along guidewire 10.

Various aspects of the invention are described in greater detail in the following Examples, which represent embodiments of this invention, and are by no means to be interpreted as limiting the scope of this invention.

The invention claimed is:

1. A guidewire stop configured to lock a medical device onto a guidewire, said guidewire stop comprising a locking element, an actuator coupled to the locking element and a locking tube defining a proximal opening and a distal opening and wherein the locking tube is configured to receive at least a section of the guidewire and at least part of the locking element or actuator;
   wherein the locking tube defines at least one unlocking element between the proximal opening and the distal opening, wherein the at least one unlocking element is configured to unlock the medical device from the guidewire; and
   wherein the guidewire stop has at least the following four configurations:
   an initial unlocked configuration in which the guidewire stop and the medical device are movable relative to the guidewire;
   a first locked configuration in which the guidewire stop and the medical device are not movable relative to the guidewire;
   a first unlocked configuration in which the guidewire stop and the medical device are movable relative to the guidewire; and
   a second locked configuration that is different from the first locked configuration, in which the guidewire stop and the medical device are not movable relative to the guidewire.

2. The guidewire stop according to claim 1, wherein the at least one unlocking element is a hole, fissure, indentation, cavity, orifice, window, gap, dent, cut, puncture or perforation in the locking tube, and wherein the at least one unlocking element has a size and shape allowing the at least one unlocking element and the locking element to be engaged with one another.

3. The guidewire stop according to claim 1, wherein the locking tube is configured to receive at least part of the medical device.

4. The guidewire stop according to claim 1, wherein at least one element of the guidewire stop is configured to be coupled to the medical device.

5. The guidewire stop according to claim 4, wherein the locking tube is configured to be coupled to the medical device.

6. The guidewire stop according to claim 1, wherein the locking element is a tapered locking element.

7. The guidewire stop according to claim 6, wherein the actuator is operatively coupled to a tip portion of the tapered locking element by a separable screw connection.

8. The guidewire stop according to claim 1, wherein the locking element is movable in the proximal direction from the initial unlocked configuration to the first locked configuration and from the first locked configuration to the first unlocked configuration by pulling on the actuator in the proximal direction.

9. The guidewire stop according to claim 1, wherein the locking element is movable in the proximal direction by a rotary movement of the actuator.

10. The guidewire stop according to claim 1, wherein the locking element and the actuator are formed as an integral unit.

11. The guidewire stop according to claim 1, wherein the actuator comprises a pulling wire extending in a longitudinal direction.

12. The guidewire stop according to claim 11, wherein the pulling wire is uncoupled from the locking element when a pulling force applied longitudinally in a proximal direction exceeds a predetermined value.

13. The guidewire stop according to claim 1, wherein the locking tube, the locking element, the actuator or any combination thereof is configured to be coupled to the medical device.

14. The guidewire stop according to claim 1, wherein the medical device is an embolic filter.

15. The guidewire stop according to claim 1, wherein the locking tube includes a plurality of unlocking elements.

16. A guidewire stop configured to lock a medical device onto a guidewire, said guidewire stop comprising a locking element, an actuator coupled to the locking element and a locking tube and wherein the locking tube is configured to receive at least a section of the guidewire and at least part of the locking element or actuator;
   wherein the locking tube comprises a proximal opening and a distal opening and defines at least one unlocking element between the proximal opening and the distal opening, the at least one unlocking element configured to unlock the medical device from the guidewire; and
   wherein the guidewire stop has at least the following five configurations:
   an initial unlocked configuration in which the guidewire stop and the medical device are movable relative to the guidewire;
   a first locked configuration in which the guidewire stop and the medical device are not movable relative to the guidewire;
   a first unlocked configuration in which the guidewire stop and the medical device are movable relative to the guidewire;
   a second locked configuration that is different from the first locked configuration, in which the guidewire stop and the medical device are not movable relative to the guidewire; and
   a second unlocked configuration that is different from the first unlocked configuration in which the guidewire stop and the medical device are movable relative to the guidewire.

\* \* \* \* \*